United States Patent [19]

Sherman et al.

[11] Patent Number: 4,848,349
[45] Date of Patent: Jul. 18, 1989

[54] SUBSTANCE AND METHOD FOR MEASURING HEPATIC BLOOD FLOW

[76] Inventors: Igor A. Sherman, 47 Edith Drive, Toronto, Ontario, Canada, M4R 1Y9; Murray M. Fisher, 76 Braeside Road, Toronto, Ontario, Canada, M4N 1X7

[21] Appl. No.: 43,812
[22] Filed: Apr. 29, 1987
[51] Int. Cl.$^4$ .............................. A61B 5/00; C07J 9/00
[52] U.S. Cl. .................................. 128/633; 250/461.2; 260/397.1
[58] Field of Search ............... 128/633, 634, 654, 665, 128/691; 250/461.1, 461.2; 260/397.1; 514/175

[56] References Cited

U.S. PATENT DOCUMENTS 4,172,085 10/1979 Monks et al. .................... 260/397.1
4,220,598 9/1980 Hixson, Jr. et al. ............. 260/397.1

FOREIGN PATENT DOCUMENTS 3238353 4/1984 Fed. Rep. of Germany ... 250/461.2

Primary Examiner—William E. Wayner
Attorney, Agent, or Firm—Smart & Biggar

[57] ABSTRACT

The invention discloses a new class of compounds, namely fluorescently labelled bile acids, as well as processes for their production. These compounds may be used for diagionstic and research purposes in humans and animals. The fluorescently labelled bile acids may be used: to indirectly measure hepatic blood flow; to measure gastrointestinal absorption of bile acids or salts; for the localization of nodules in tissues which absorb bile acids; and for the in vitro and in-vivo analysis of cellular or microcirculatory transport or other phenomena.

8 Claims, No Drawings

SUBSTANCE AND METHOD FOR MEASURING HEPATIC BLOOD FLOW

SPECIFICATION

This invention relates to medical diagnostic procedures and the analysis of physiological function in humans and animals. The invention discloses a new class of compounds as well as processes for their production.

The use of chemical substances in humans and animals for diagnostic and research purposes is known. Such substances include dyes, fluorescent compounds and radioactive compounds. Researchers have utilized these substances in humans and animals to study organ function, organ structure, microcirculation and transport mechanisms at both the tissue and cellular levels. In the case of human and animals livers, the hepatic transport of various molecules, including bile acids has been extensively studied using a number of techniques. Considerable insight into the pharmacokinetics of hepatic uptake processes has been provided by the use of indicator-dilution techniques. While this approach has permitted calculation of perameters such as the Tmax and the "initial" uptake velocity, no measurement of actual transport times has been possible.

Indirect estimates of liver blood flow rely on measuring the concentration of substances introduced into the blood which are removed by the liver in proportion to hepatic blood flow. Several compounds have been used to measure hepatic blood flow, however all of them have certain disadvantages. The most commonly used compound, indocyanine green, is very expensive, its detection may be affected by certain other molecules present in blood and its hepatic uptake may change in pathological states.

The present invention embodies new chemical substances, processes for their production, new uses for the chemical substances and methods for such uses which overcome difficulties and disadvantages of prior art chemical substances, processes, uses, methods and procedures familiar to those skilled in the art.

The present invention contemplates the use of new chemical substances for measuring physiological functions including hepatic blood flow. The new chemical substances are fluorescently labelled bile acids formed by reacting fluorescent compounds such as fluorescein isothiocyanate with bile acids. Tracer amounts of these fluorescently labelled bile acids can be utilized for the indirect measurement of hepatic blood flow. These same fluorescently labelled bile acids can also be used for other diagnostic and research procedures such as measurement of gastrointestinal absorption of bile acids and for facilitating localization of neoplastic and/or preneoplastic nodules in the liver and other tissues. Furthermore, these fluorescently labelled bile acids may be used for in-vitro and in-vivo research studies of transport and other phenomena at the microcirculatory level as well as the cellular level.

Accordingly, the present invention provides a fluorescently labelled bile acid having the following chemical structure:

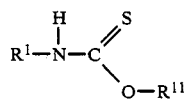

where $R^1$ is fluorescein and $R^{11}$ is a bile acid, joined to the oxygen via the third carvon on the A ring of the bile acid.

The present invention further provides for a fluorescently labelled bile acid having the following chemical structure:

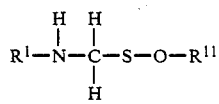

where $R^1$ is fluorescein and $R^{11}$ is a bile acid joined to oxygen via the third carbon on the A ring of the bile acid.

The present invention still further provides a process for conjugating bile acid with a fluorescent compound comprising the steps of:

(a) dissolving in a suiable solvent equimolar amounts of a bile acid and a fluorescent compound;

(b) heating the resulting mixture until the bile acid and the fluorescent compound react to form a conjugate;

(c) precipitating the conjugate out of solution;

(d) dissolving the conjugate precipitate in a solvent suitable for running on a thin-layer chromatography plate;

(e) running the resulting solution on a preparative thin-layer chromatography plate;

(f) removing the resulting conjugate from the chromatography plate and extracting with a suitable solvent;

(g) further purification of the resulting extract by centrifugation; and (h) storage of the pure fluorescent compound bile acid conjugate in the absence of light.

The present invention still further provides a process for conjugating bile acid with a fluorescent compound comprising the steps of:

(a) dissolving in a suitable solvent equimolar amounts of the fluorescent compound and a bile acid;

(b) heating the resulting mixture until the bile acid and the fluorescent compound react to form a conjugate;

(c) dissolving the conjugate mixture in a mobile phase suitable for high pressure liquid chromatography; and (d) separating the mixture on a high pressure liquid chromatography column to provide a pure fluorescent compound bile acid conjugate which is then collected as an effluent at the appropriate time.

The present invention still further provides a diagnostic procedure for humans and animals comprising the use of fluorescently labelled bile acid to indirectly measure hepatic blood flow.

The present invention still further provides a diagnostic procedure for humans and animals comprising the use of fluorescently labelled bile acid to measure gastrointestinal absorption of bile acids or salts.

The present invention still further provides a diagnostic procedure for humans and animals comprising the use of fluorescently labelled bile acid for the localization of nodules in tissues which absorb bile acids.

The present invention still further provides a diagnostic or research procedure for human and animal studies comprising the use of fluorescently labelled bile acid for the in-vitro and in-vivo analysis of cellular or microcirculatory transport or other phenomena.

The present invention was partially particularized in an article, by the inventors hereof, in Vol. 6, No. 3, pp 444-449 issue of HEPATOLOGY, available to the public in May of 1986.

The inventors have found that fluorescently labelled bile acids are well suited for diagnostic and research purposes in a variety of application in view of their following inherent advantages:

(a) they have physiological properties similar to naturally present bile acids. Most are nontoxic and physiologically innocuous in small quantities;

(b) they have a hepatic extraction ratio in excess of 90% in a single pass through the liver;

(c) they are easy to detect at parts per billion concentrations by fluorimetric techniques;

(d) they are relatively inexpensive to produce;

(e) they undergo an enterohepatic circulation similar to that of natural bile acids; and (f) they can be used for diagnostic purposes in millimolar quantities (if necessary) that will not affect the physiological status of the subject.

The fluorescently labelled bile acids may be produced by conjugating fluorescein isothiocyanate (FITC) or other suitable fluorescent compound, with a bile acid and then separating the pure fluoresceinated monomer by either thin layer chromatography or preparative high pressure/performance liquid chromatography (HPLC). Although the processes particularized herein refer to FITC, it should be understood that other fluorescent substances such as Rhodamine B isothiocyanate or various methylcoumarins may be conjugated to bile acids and utilized as set out herein.

Bile acids are species specific in that different species of animals have characteristically different bile acids. In man, several different biile acids are known. Examples of these are:

Cholic Acid (3α,7α,12α-Trihydroxy-5β-cholan-24-oic acid)

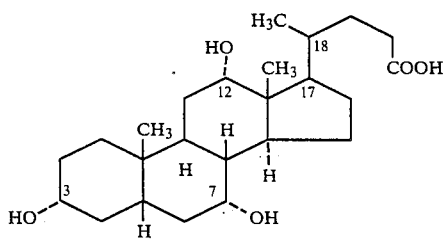

Chenodeoxycholic Acid (3,7-Dihydroxycholan-24-oic acid)

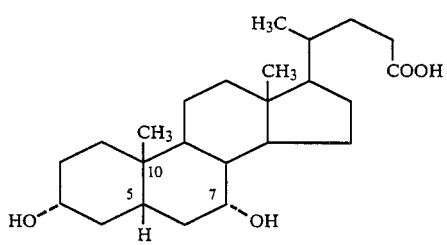

Deoxycholic Acid (3α,12α-dihydroxy-5β-cholanic acid)

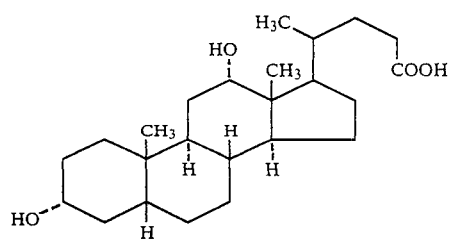

Lithocholic Acid (3α-hydroxycholanic acid)

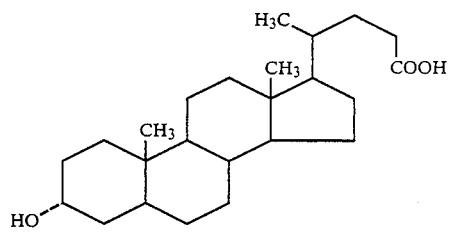

All bile acids can be conjugated with FITC. However, some bile acids present in man are toxic, but their natural presence in small quantities is such as not to affect the health of mankind. The toxic bile acids are the monohydroxybile acids (i.e. lithocholic) and obviously they are not suitable for use in diagnostic procedures as the quantities may result in toxic effects in the subject. These could be used for research purposes.

Two processes for the manufacture of the fluorescently labelled bile acids are set out hereinafter. Although these processes refer to the use of FITC, it should be understood that other fluorescent compounds may similarly be employed. The steps common to both processes are the dissolution in a suitable solvent of equimolar amounts of a bile acid and fluorescein isothiocyanate and thereafter heating the resulting mixture until the bile acid and the fluorescein isothiocyanate react to form a conjugate. The solvent must be one in which both the bile acid and fluorescein isothiocyanate are soluble and furthermore be free of water which will react with FITC. One such suitable solvent is methyl sulfoxide. The resulting mixture may be heated to the boiling point of the solvent used. Heating speeds up the reaction resulting in the conjugate. When the methyl sulfoxide is used as the suitable solvent, the mixture may be heated and maintained at 100° C. for four hours and then allowed to cool to room temperature. From this point on, the two processes differ.

In the first process the conjugate is precipitated out of solution. This can be accomplished by mixing the solution with a polar liquid in which the solubility of the conjugate is low. For example, the conjugate may be precipitated out of solution by pouring the conjugate solution, while stirring, into 20 volumes of cold water. Once the conjugate has precipitated it may be removed from the solution by filtration or by centrifugation and removal of the supernatant. After the conjugate precipitate is isolated, it is dissolved in a solvent suitable for running on a thin-layer chromatography (TLC) plate. Solvents suitable for running on a TLC plate are well known to those skilled in the art. An example of such a solvent is methanol. Next, the solvent containing the fluorescently labelled bile acid conjugate is run on a preparative thin-layer chromatography plate. For this purpose, a suitable solution, such as chloroform:methanol in the proportions of 3:1 may be used. After isolation, the conjugate is scraped from the plate and extracted with another suitable solvent such as methanol. The resulting extract is further purified by centrifugation, for example, at 1000 rpm for 10 minutes. The supernatant is removed and may be dried under nitrogen. The resulting fluorescein isothiocyanate-bile acid conjugate is stored in a cool, moisture proof container in the absence of light. The absence of light is important since fluorescent molecules react with light, and thereby may cause the conjugate to dissociate or may result in the quenching of fluorescence. This first process has been partially particularized in the above mentioned HEPATOLOGY article.

In the second process, the reaction mixture is dissolved in a mobile phase suitable for high pressure liquid chromatography (HPLC). The mobile phase may consist of 70% methanol/30% water with the pH adjusted to pH 2.5 with an acid such as phosphoric acid. The mixture is then separated on a HPLC column and pure fluorescein isothiocyanate-bile acid conjugate is collected as an effluent at the appropriate time (when the FITC-bile acid comes along the column). The latter process provides higher yield and is less time and labour intensive than the process first described. The latter process can also be easily automated for continuous separation of the pure product. The first described process has the advantage of not requiring the fairly sophisticated HPLC equipment.

Fluorescein isothiocyanate-bile acids (hereinafter sometimes referred to as "FITC-bile acid"), as well as other fluorescently labelled bile acids can be used to measure the nutritional liver blood flow in the following way. The FITC-bile acid is introduced into the blood stream via oral dosage, IV dose or constant infusion. Preferably, a single IV bolus injection of FITC-bile acid ($\approx 2$ micromoles/kg body weight) is given. Serial blood samples are taken over the period of time of up to twenty minutes (total of 3 to 5 samples to be taken following injection). Liver blood flow may be determined by analyzing the elimination rate of the fluorescently labelled bile acid from the plasma. Liver blood flow may be calculated using the following equations:

$$Q_p = \frac{M}{k \int_0^\infty c(t)dt} \; ; \; Q_L = \frac{Q_p}{1 - Htc}$$

where $Q_L$ is nutritional liver blood flow; M is the amount of FITC-bile acid injected; k is a constant (=1 for 100% extraction, 0.9 if extraction is 90%); and $c(t)$ is the monoexponentially declining concentration of injected fluorescently labelled bile acid in blood and is obtained by fitting a monoexponential curve to concentration values obtained from individual plasma samples; $Q_p$ is plasma clearance of fluorescently labelled bile acid. Alternatively, the liver blood flow may be determined by measuring the steady state equilibrium of the fluorescently labelled bile acid input into the blood stream, and the uptake by the liver of the fluorescently labelled bile acid. If input into blood is charted against hepatic uptake, then the steady state equilibrium will appear as a plateau and this will identify the rate of hepatic blood flow, using the following equations:

$$Q_p = \frac{m_o}{C_p K} \; ; \; Q_L = \frac{Q_p}{1 - Htc}$$

where $m_o$ is the rate of infusion of the fluorescently labelled bile acid in $\mu$moles/sec; $C_p$ is steady state plasma concentration of the fluorescently labelled bile acid in $\mu$moles/cc; K is a constant (equal to hepatic extraction ratio of the fluorescently labelled bile acid); $Q_p$ is plasma clearance of the fluorescently labelled acid; $Q_L$ is liver blood flow; and Htc is hematocrit.

Fluorescently labelled bile acids can also be used to measure gastrointestinal absorption of bile acids. Presently, radioactively labelled bile acids are used for this purpose. Fluorescently labelled bile acids have the advantages of being stable, less expensive, more simply detected, and not radioactive. A single oral dose may be given and subsequently the stools analysed for the presence of bile acid, or blood samples taken to determine the concentration of fluorescent bile acid.

Fluorescently labelled bile acids may also be used to facilitate the detection of neoplastic and preneoplastic nodules in the liver during surgery. 5 to 10 minutes following a single IV dose of fluorescently labelled bile acid the liver can be illuminated with blue light (wavelength between 350 to 390 nm) and observed through a green filter (transmitting light with a wavelength over 510 nm). Fluorescein absorbs blue light and emits green light. Nodules will appear as black areas on a green background because their uptake of bile acids is lower than that of normal liver tissue. Detection of nodules down to 0.5 mm diameter is possible. Use of optical magnifying devices will further lower the detection limit. A similar technique may apply for tumor detection in other tissues and organs, particularly skin.

Fluorescently labelled bile acids may also be used for the visualization of blood flow in skin vessels, nailfold capillaries, eye microvasculature etc., in order to assess vascular angiopathies in these tissues, detect preulcerative conditions or monitor the progress of treatment of vascular related disorders.

The use of FITC bile acid for measuring liver blood flow has been tested in a dog. The following experimental protocol was followed.

15 $\mu$moles of FITC-labelled glycocholic bile acid (FITC-GC) in 2 ml normal saline were injected into a 9 kg dog. Serial blood samples were taken into heparinized containers at 2, 4, 6, 8, and 10 minutes following the initial injection. The samples were then centrifuged for 5 minutes and the plasma collected. The concentration of FITC-GC in each plasma sample was measured with a PERKIN-ELMERS* spectrophlourimeter, using a previously determined calibration curve for FITC-GC solutions in plasma.

*trade mark

The concentration values in plasma serial samples exhibited monoexponential decline. Therefore plasma clearance was calculated as $$Q_p = \frac{M}{k \int_0^\infty c(t)dt}, \text{ where } c(t) = C_o e^{-\frac{t}{\tau}},$$

M-amount of material injected and k=const. (k=1 for 100% extraction, 0.9 for 90% extraction), thus $$Q_p = \frac{M}{kC_o\tau},$$

where $$\frac{1}{\tau}$$

is the slope of the line for concentration vs. time plot on a semi-log paper, and Co is the initial concentration (log $C_o$ is determined as an intercept of the plot with the concentration axis). For the purpose of calculating plasma clearance, k was assumed to equal 0.9.

Liver blood flow was then calculated from the plasma clearance value using the previously determined blood hematocrit (Htc) value as follows:

$$\text{Liver blood flow} = \frac{Q_p}{1 - Htc}$$

In this particular animal liver blood flow was found to be 194 ml/min, which is in agreement with the expected liver blood flow in an animal of this size.

With respect to the chemical structure of the fluorescently labelled bile acids, it has been determined using nuclear magnetic resonance studies that the conjugate consists of one fluorescein isothiocyanate molecule attached to one bile acid molecule (i.e. sodium glycocholate), at the third carbon position of the A-ring of the bile acid (as set out below). No dimers or polymers of the conjugate were found.

Below is the general structure of a trihydroxy bile acid.

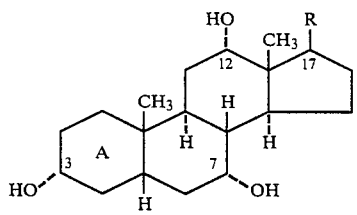

Below is the structure of fluorescein isothiocyanate (FITC).

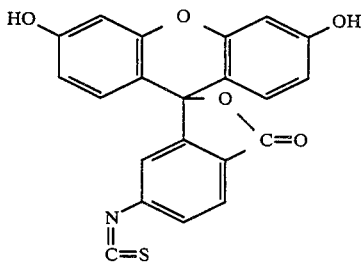

The product of the reaction between FITC and a bile acid is most likely:

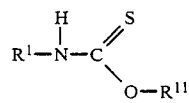

where $R^1$ is fluorescein and $R^{11}$ is the bile acid (joined at C3). Another possibility is the creation of a sulfur ester, where sulfur instead of carbon reacts with the bile acid C3 hydroxyl group.

The product of this reaction would be:

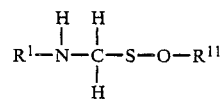

where $R^1$ is fluorescein and $R^{11}$ is a bile acid joined to oxygen via the third carbon on the A ring of the bile acid.

In experiments conducted with fluorescein isothiocyanate-sodium glycocholate (FITC-GC) it was found that the FITC-GC had the same effects on bile flow, sinusoidal blood flow, blood pressure and heart rate of rats and hamsters as equimolar amounts of sodium glycocholate. In another group of experiments, FITC-GC was injected intraduodenally and bile samples collected for a period of two hours. More than 90% of the injected conjugate was excreted in the bile. Reinjection into the duodenum of the bile collected in these experiments again resulted in almost complete elimination of the injected conjugate via bile. These experiments therefore demonstrate that FITC-GC produces the same physiological effects as sodium glycocholate and also undergoes an enterohepatic circulation. It is these characteristics of fluoresceintly labelled bile acids which make them valuable as diagnostic agents and research tools.

The embodiments of the invention in which an exclusive property or privilege is claimed are defined as follows:

1. A diagnostic procedure for humans and animals comprising the use of fluorescently labelled bile acid to indirectly measure hepatic blood flow.

2. The diagnostic procedure of claim 1 comprising the steps of:
   (a) introducing the fluorescently labelled bile acid into the blood stream; and
   (b) thereafter measuriang the elimination rate of the fluorescently labelled bile acid from the blood.

3. The diagnostic procedure of claim 1 comprising the steps of:
   (a) introducing the fluorescently labelled bile acid into the blood stream at a constant rate for a period of time required to achieve steady state; and
   (b) thereafter measuring the steady state concentration of the fluorescently labelled bile acid.

4. The diagnostic procedure of claim 2 wherein:
   (a) the human or animal is given a single IV bolus injection of fluorescently labelled bile acid;
   (b) serial blood samples are taken at intervals following the bolus injection and the concentration of fluorescently labelled bile acid therein is determined; and (c) hepatic blood flow is calculated from the rate of change in blood concentration of fluorescently labelled bile acid.

5. The diagnostic procedure of claim 4 wherein hepatic blood flow is calculated using the formulae:

$$Q_p = \frac{M}{k \int_0^\infty c(t)dt} \text{ and } Q_L = \frac{Q_p}{1 - Htc}$$

where $Q_L$ is nutritional liver blood flow; M is the amount of fluorescently labelled bile acid injected; K is a constant dependant on the rate of extraction; c(t) is the monoexponentially declining concentration of injected fluorescently labelled bile acid in the blood; $Q_p$ is plasma clearance of the fluorescently labelled bile acid; and Htc is blood hematocrit.

6. The diagnostic procedure of claim 3 wherein:
  (a) the fluorescently labelled bile acid is introduced by continuous infusion at a constant rate;
  (b) the plasma concentration of the fluorescently labelled bile acid is measured from a blood sample taken after steady state equilibrium is reached;
  (c) hepatic plasma clearance is calculated using the formula:

$$Q_p = \frac{m_o}{C_p K}$$

where $m_o$ is the rate of infusion of the fluorescently labelled bile acid in $\mu$mole/sec; $C_p$ is plasma concentration of the fluorescently labelled bile acid in $\mu$moles/cc; k is a constant equal to the hepatic extraction ratio of the fluorescently labelled bile acid; and $Q_p$ is plasma clearance of the fluorescently labelled bile acid;

(d) hepatic blood flow is calculated using the formula:

$$Q_L = \frac{Q_p}{1 - Htc}$$

where $Q_L$ is hepatic blood flow and Htc is blood hematocrit.

7. The diagnostic procedure of claim 5 or 6 wherein the fluorescently labelled bile acid is fluorescein isothiocyanate-bile acid.

8. A research procedure for human and animal studies comprising the use of a compound containing fluorescently labelled bile acid for the in-vivo analysis of cellular or microcirculatory transport or other phenomena.

* * * * *